(12) United States Patent
Jörnéus

(10) Patent No.: US 6,174,166 B1
(45) Date of Patent: Jan. 16, 2001

(54) ARRANGEMENT FOR AN IMPLANT SYSTEM

(75) Inventor: Lars Jörnéus, Frillesås (SE)

(73) Assignee: Nobel Biocare AB, Gothenburg (SE)

( * ) Notice: Under 35 U.S.C. 154(b), the term of this patent shall be extended for 0 days.

(21) Appl. No.: 09/194,741

(22) PCT Filed: Jun. 12, 1997

(86) PCT No.: PCT/SE97/01034

§ 371 Date: Jan. 22, 1999

§ 102(e) Date: Jan. 22, 1999

(87) PCT Pub. No.: WO98/01081

PCT Pub. Date: Jan. 15, 1998

(30) Foreign Application Priority Data

Jul. 4, 1996 (SE) .................................................. 9602636

(51) Int. Cl.[7] .................................................. A61C 8/00
(52) U.S. Cl. ........................... 433/172; 433/173; 433/174
(58) Field of Search ................................ 433/173, 174, 433/175, 220, 221, 169, 172, 177

(56) References Cited

U.S. PATENT DOCUMENTS

| 4,850,870 | * | 7/1989 | Lazzara et al. | 433/174 |
|---|---|---|---|---|
| 4,850,873 | * | 7/1989 | Lazzara et al. | 433/220 |
| 4,988,298 | * | 1/1991 | Lazzara et al. | 433/173 |
| 5,040,983 | * | 8/1991 | Binon | 433/173 |
| 5,145,371 | * | 9/1992 | Jorneus | 433/173 |
| 5,667,382 | * | 9/1997 | Sutter et al. | 433/172 |
| 5,695,335 | * | 12/1997 | Haas et al. | 433/173 |
| 5,725,377 | * | 3/1998 | Lemler et al. | 433/173 |
| 5,951,287 | * | 9/1999 | Hawkinson | 433/173 |

OTHER PUBLICATIONS

Brånemark et al., Osseointegrated Implants in the Treatment of the Edentulous Jaw, Experience from a 10–year period, Laboratory of Experimental Biology, Department of Anatomy, University of Göteborg, Sweden, 1977, pp. 33–34.

* cited by examiner

Primary Examiner—Pedro Philogene
(74) Attorney, Agent, or Firm—Pollock, Vande Sande & Amernick

(57) ABSTRACT

An arrangement for an implant system. A fixture includes an internal thread, a contact plane, a spanner attachment part, and a recess arranged in the spanner attachment part. A spacer screw includes an external thread and a cylindrical portion arranged above the external thread. The external thread of the spacer screw can be screwed securely to the internal thread of the fixture. The cylindrical portion engages the recess of the fixture when the spacer screw is tightened in the fixture. A spacer element contacts the contact plane of the fixture. A unit can be screwed securely to the spacer screw.

15 Claims, 1 Drawing Sheet

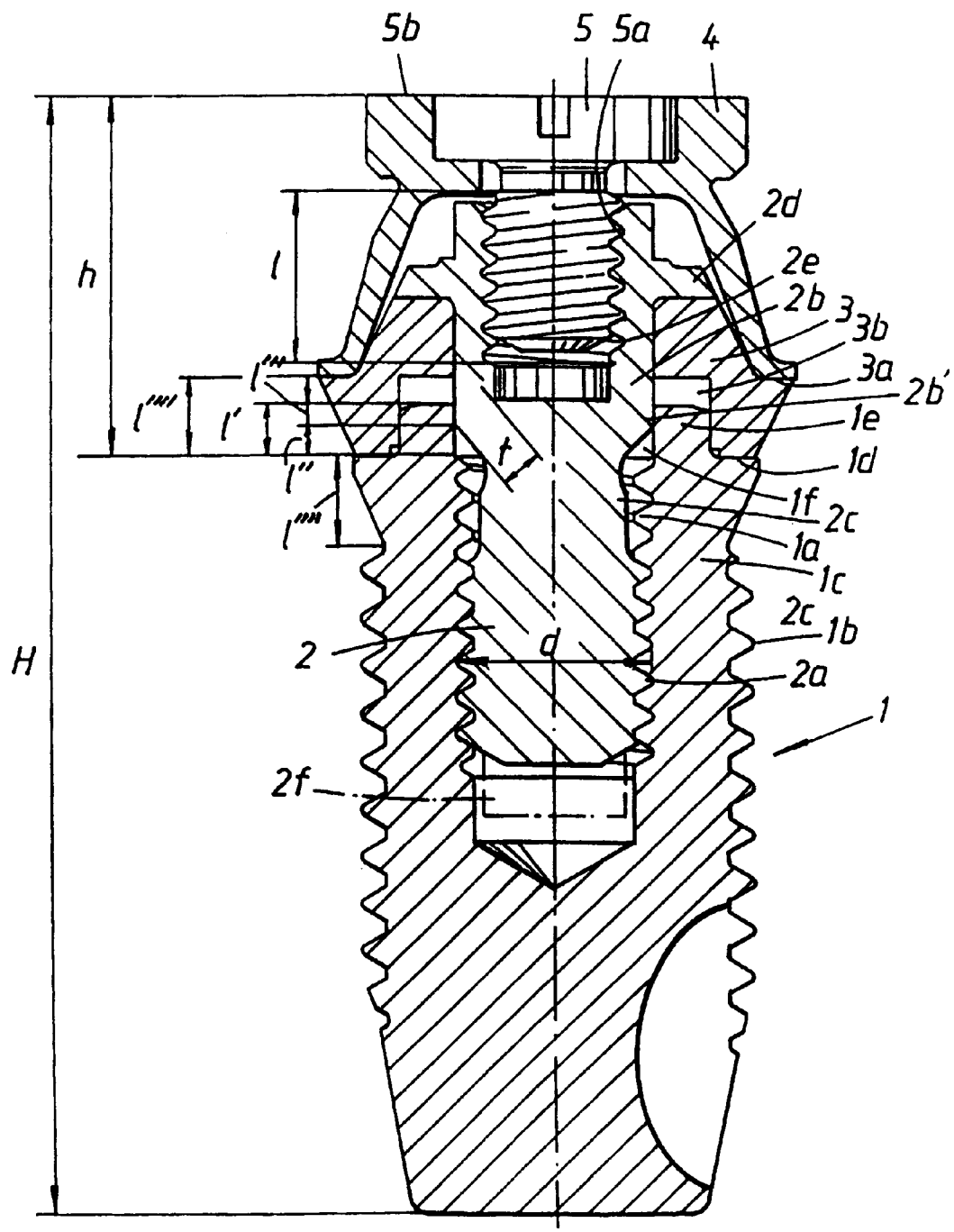

ARRANGEMENT FOR AN IMPLANT SYSTEM

FIELD OF THE INVENTION

The present invention relates to an arrangement for an implant system which includes a fixture (anchoring element) and a spacer screw which can be screwed securely to the fixture, with an associated spacer element. The present invention also includes a unit, for example a cylinder (prosthesis structure), which can be screwed securely to the spacer screw. The fixture has an internal thread which the spacer screw can be screwed into by means of a corresponding external thread. The fixture also has a contact plane for the spacer element, and a spanner attachment part. The said spacer screw is designed with a cylindrical portion located above its external thread.

Implant systems of the type specified above are already known and are sold by Nobel Biocare on the open market.

BACKGROUND OF THE INVENTION

In implant systems of the type specified above, it is necessary to be able to combine a low structural height with the required mechanical strength of the various components of the system. Thus, it is necessary, in some cases, to provide the lowest possible structural height between the contact plane of the fixture and the top surface of the prosthesis unit (cylinder) without neglecting the mechanical strength of, for example, the prosthetic securing screw. The aim of the invention is to solve this problem, among others.

It is also important to be able to achieve the greatest possible strength in the upper parts of the fixture wall. This is also afforded by means of the invention.

Implant systems of the type in question have small dimensions and it is necessary to be able to provide good guidance functions which ensure thread engagement of each respective screw in the initial stage. It also has to be possible to facilitate the tightening function itself. This is achieved as an added effect in the present invention.

It is also possible, as regards the subject of the invention, to make additional improvements which increase still further the initial thread engagement function.

SUMMARY OF THE INVENTION

The feature which can principally be regarded as characterizing an arrangement according to the invention is that the fixture or the anchoring element is arranged with a recess which is located in the spanner attachment part and in which the cylindrical portion of the spacer screw can be completely or partially engaged when the spacer screw is drawn tight in the fixture or the anchoring element.

In one embodiment, the depth of the recess, and thus the degree to which the cylindrical portion can be engaged in the recess, is arranged such that it essentially corresponds to 2–4 thread turns of the internal thread of the anchoring element. The engagement of the cylindrical portion in the recess is dependent, inter alia, on the height of the spacer element. In a further embodiment, an external thread, arranged on a holding screw for securing the unit in the spacer screw, has an extension function which corresponds to the engagement of the cylindrical portion in the recess of the spanner attachment part, compared to the case where there is no recess in the spanner attachment part. The extension of the external thread ensures a desired strength function for the holding screw and the implant system as such.

The diameter of the recess slightly exceeds the diameter of the external threads on the spacer screw, which means that the recess exercises an initial guidance function for the spacer screw as it is being screwed into the internal thread of the anchoring element. The spacer screw can moreover be provided with a tap at its free end for affording an important guidance function in the recess as the spacer screw is being screwed into the fixture.

In one embodiment, the cylindrical portion of the spacer screw merges into an unthreaded portion which in turn merges into the external thread of the spacer screw.

In accordance with the concept of the invention, the recess entails the absence of internal thread turns in the upper parts of the fixture. The absence of thread turns means that the fixture, in the upper parts, remains essentially unloaded by impinging forces when the spacer screw is being tightened in the fixture. Moreover, in one embodiment, the recess in the fixture has a maximum depth which guarantees mechanical strength in the wall portion of the fixture in the upper parts where internal thread turns in the fixture themselves form a reinforcement of the wall portion, compared to the case where there are no internal thread turns. The depth of the recess is chosen within a range of 0.5–2.0 mm, and is preferably about 1.0 mm. The total height of the fixture, spacer element and unit is chosen within the range of 10–20 mm. The height between the top surface of the unit and the contact plane of the fixture for the spacer element is 4–8 mm.

By means of the invention it is possible to construct implant systems which are suitable for different purposes and which have a high degree of adaptability to existing cortical dentine layers of different thicknesses. The prosthesis structure can be given a reliable anchoring function even when there is a requirement for a low structural height between the contact plane of the fixture and the position or level at which the prosthesis structure is secured.

BRIEF DESCRIPTION OF THE DRAWINGS

A presently proposed embodiment of an arrangement having the characteristic features of the invention will be described hereinbelow with reference to the attached drawing, which: shows a vertical section through an implant system with fixture, spacer screw and spacer element, and a unit (cylinder) which can be screwed securely into the screw for supporting the prosthesis structure (not shown).

DETAILED DESCRIPTION OF THE INVENTION

In the FIGURE, reference label 1 designates a fixture or anchoring element which is intended to be screwed securely into dentine (not shown) in a know manner. The anchoring element is assumed to be known and will therefore not be described in detail in terms of its structure and function. The anchoring element has an internal thread 1a, an external thread 1b and a wall portion 1c. It also has a contact plane 1d and a spanner attachment part 1e.

A so-called spacer screw 2 can be screwed into the element 1 via an external thread 2a which can interact with the internal thread 1a of the fixture 1. The spacer screw has, in addition to the screw part 2, a cylindrical portion 2b which merges into an unthreaded portion 2c, which in turn merges into the external thread 2a. A spacer element 3 belonging to the spacer screw 2 is placed between a projecting flange 2d of the screw and the contact plane 1d of the fixture 1. The height of the spacer element can be chosen on a case-by-case basis. The spacer element has a bearing surface 3a for a unit 4 (a gold cylinder) which is intended to support a prosthesis structure (tooth replacement, crown, etc.) which is not shown here.

In its upper parts, the spacer screw has an internal thread 2e by means of which the unit can be screwed securely by means of a holding screw 5 via an external thread 5a which corresponds to the internal thread 2e. This securing is also known per se and will not be described in detail here, other than to say that when the screw 5 is tightened, the unit 4 clamps the spacer element against the fixture 1 and that the components included in the implant system are held together in this way. It will be appreciated that the length 1 of the thread 5a constitutes a critical function for the securing of the components in the implant system.

The length 1 can be kept to an optimum by using a recess if, in which a part 2b' of the cylindrical portion 2b can be engaged. The recess 1f and the cylindrical portion 2b/2b' are cylindrical in the illustrative embodiment, and the diameter of the recess If slightly exceeds the diameter of the cylindrical portion 2b/2b'.

The recess if has been created by boring out internal thread turns 1a in the upper parts. In the illustrative embodiment, 2 to 4 thread turns have been bored out. The depth of the recess is shown by 1' and corresponds essentially to the 2 to 4 thread turns. The spacer screw can function for different heights of the spacer element. The depth of the recess is 0.5 to 2.0 mm, preferably about 1 mm. The screw can be engaged further by a distance 1" (where the spacer element has a lower height) and, in the screwing example shown here, is engaged by a distance 1'".

By means of the arrangement, a material thickness t in the spacer screw, between the recess for the thread 2e and the transition between the cylindrical portion 2b and the unthreaded part 2c of the spacer screw, can be kept to a value which is acceptable from the point of view of strength, despite an appreciable length 1 of the thread 5a of the holding screw 5. The depth of the recess is also determined by a value 1"" for the upper level of the internal thread 1a and the level of the external thread 1b. If further turns of the internal thread 1a were bored out, this would result in a weakening of the upper parts of the wall 1c, which would cause difficulties from the point of view of strength when the spacer screw is being tightened. In the case shown here, the greatest stresses occur at a position 3 to 4 thread turns below the recess, by virtue of the unthreaded portion 2c.

The invention affords a low structural height h between the contact plane 1d of the fixture and the top surface 5b of the unit 4, which low structural height h can be reduced by the distance 1'".

The diameter of the recess 1f slightly exceeds the diameter d of the internal thread 1a. The recess can in this case serve as a guide for the spacer screw. A further improved guidance function can be obtained with a tap 2f at the free end of the spacer screw. The total height of the system is shown by H and is chosen within the range of 6–13 mm, and is preferably about 10 mm. The spacer element 3 has an internal recess 3b which corresponds to the spanner attachment 1e which fixes the spacer element in terms of its angle of rotation. The flange 2d on the spacer element can be displaced relative to the spacer screw as the spacer screw is being tightened in the fixture.

The invention is not limited to the embodiment which is shown hereinabove by way of example, and instead can be modified within the scope of the attached patent claims and the inventive concept.

What is claimed is:

1. An arrangement for an implant system, comprising:
    a fixture comprising an internal thread, a contact plane, a spanner attachment part, and a recess arranged in the spanner attachment part;
    a spacer screw comprising an external thread and a cylindrical portion arranged above the external thread, wherein the external thread of the spacer screw can be screwed securely to the internal thread of the fixture, and wherein the cylindrical portion engages the recess of the fixture when the spacer screw is tightened in the fixture;
    a spacer element contacting the contact plane of the fixture; and
    a unit that can be screwed securely to the spacer screw.

2. The arrangement according to claim 1, wherein the fixture comprises an anchoring element.

3. The arrangement according to claim 1, wherein the unit comprises a cylinder.

4. The arrangement according to claim 1, wherein the unit comprises a prosthesis structure.

5. The arrangement according to claim 1, wherein a depth of the recess in the fixture and an extent to which the cylindrical portion of the spacer screw can be engaged in the recess corresponds essentially to 2–4 turns of the internal thread on the fixture.

6. The arrangement according to claim 1, further comprising:
    a holding screw comprising an external thread for holding the unit securely in the spacer screw, the external thread comprising an extension that corresponds to a degree of engagement of the cylindrical portion of the spacer screw in the recess of the spanner attachment part of the fixture, compared to a case wherein the spanner attachment part does not include a recess, which ensures a desired strength function of the holding screw.

7. The arrangement according to claim 1, wherein a diameter of the recess in the spanner attachment part slightly exceeds a diameter of the external thread of the spacer screw, whereby the recess guides the spacer screw when the spacer screw is being screwed into the internal thread of the fixture.

8. The arrangement according to claim 1, wherein the spacer screw comprises a tap at a free end for guiding the spacer screw as when the spacer screw is being screwed into the fixture.

9. The arrangement according to claim 1, wherein the cylindrical portion of the spacer screw merges into an unthreaded portion which in turn merges into the external thread on the spacer screw.

10. The arrangement according to claim 1, wherein upper parts of the fixture do not include a thread, whereby the upper parts of the fixture remain essentially unloaded by impinging forces when the spacer screw is being tightened in the fixture.

11. The arrangement according to claim 10, wherein the upper parts of the fixture essentially correspond to the spanner attachment part of the fixture.

12. The arrangement according to claim 1, wherein the recess in the spanner attachment part of the fixture has a maximum depth that guarantees mechanical strength in a wall portion at upper parts of the fixture where the internal thread in the fixture forms a strengthening of the wall portion compared to the case where no internal thread exists.

13. The arrangement according to claim 12, wherein a depth of the recess is 0.5–2.0 mm.

14. The arrangement according to claim 12, wherein a depth of the recess is about 1.0 mm.

15. The arrangement according to claim 1, wherein a degree of engagement of the cylindrical portion of the spacer screw in the recess of the spanner attachment part of the fixture depends upon a height of the spacer element.

* * * * *